(12) United States Patent
Rast et al.

(10) Patent No.: US 7,977,484 B2
(45) Date of Patent: Jul. 12, 2011

(54) CRYSTALLINE FORM OF CYANO-1-CYCLOPROPY1-7-1S,6S-2,8-DIAZABICYCLO[4.3.0]NONAN-8-YL)-6-FLUORO-1,4-DIHYDRO-4-OXO-3-QUINOLINE CARBOXYLIC ACID

(75) Inventors: Hubert Rast, Leverkusen (DE); Iris Heep, Köln (DE); Alfons Grunenberg, Dormagen (DE); Werner Hallenbach, Monheim (DE); Jordi Benet-Buchholz, Altafulla (ES)

(73) Assignee: Bayer Animal Health GmbH (DE)

( * ) Notice: Subject to any disclaimer, the term of this patent is extended or adjusted under 35 U.S.C. 154(b) by 893 days.

(21) Appl. No.: 11/547,420

(22) PCT Filed: Mar. 19, 2005

(86) PCT No.: PCT/EP2005/002953
§ 371 (c)(1),
(2), (4) Date: Nov. 5, 2007

(87) PCT Pub. No.: WO2005/097789
PCT Pub. Date: Oct. 20, 2005

(65) Prior Publication Data
US 2008/0125458 A1      May 29, 2008

(30) Foreign Application Priority Data

Apr. 1, 2004   (DE) .................. 10 2004 015 981

(51) Int. Cl.
*C07D 471/04* (2006.01)
(52) U.S. Cl. ........................................ 546/113
(58) Field of Classification Search .................. 546/113; 514/300
See application file for complete search history.

(56) References Cited

U.S. PATENT DOCUMENTS

| 6,323,213 | B1 | 11/2001 | Bartel et al. ............... 514/300 |
| 6,436,955 | B1 | 8/2002 | Himmler et al. ............ 514/300 |
| 6,492,391 | B1 | 12/2002 | Himmler et al. ............ 514/312 |
| 6,627,646 | B2 * | 9/2003 | Bakale et al. ............... 514/322 |
| 6,649,762 | B1 | 11/2003 | Rast et al. .................... 546/156 |
| 6,664,268 | B1 | 12/2003 | Himmler et al. ............ 514/300 |
| 6,995,170 | B1 | 2/2006 | Himmler et al. ............ 514/300 |

FOREIGN PATENT DOCUMENTS

| WO | 9731001 | 8/1997 |
| WO | 0031075 | 2/2000 |
| WO | 0031076 | 2/2000 |
| WO | 0031077 | 2/2000 |
| WO | 0052009 | 9/2000 |
| WO | 0052010 | 9/2000 |

OTHER PUBLICATIONS

Vippagunta et al., "Crystalline solids", Advanced Drug Delivery Reviews 48 (2001) 3-26.*
Ulicky et al., Comprehensive Dictionary of Physical Chemistry, NY Ellis Horwood PTR Prentice Hall, 1992, p. 21.*
Silverman, The Organic Chemistry of Drug Design and Drug Action, NY: Academic Press, Inc. 1993, 72-76.*
Rowland and Tozer. "Clinical Pharmacokinetics, etc.," 1995, p. 123.*
Jain et al., "Polymorphism in Pharmacy", Indian Drugs, 1986, 23(6) 315-329.*
Chemical & Engineering News, Feb. 2003, 32-35.*
US Pharmacopia #23, Nationa Formulary #18, 1995, 1843-1844.*
Caira, "Crystalline Polymorphism, etc.," Topics in Current Chemistry, 198, Berline Heidelberg: Springer Vertag, 1998, pp. 164-208.*
Wilbraham et al. "Organic and biochemistry . . . " p. 250-251 (1985).*
Garattini "Active drug metabolites . . . " Clin. Pharmacokinetics v.10, p. 216-227 (1985).*
Muzaffar et al., "Polymorphism, etc., " Journal of Pharmacy (Lahore) 1979, 1(1), 59-66.*
Guillory (in Brittain ed.) "Polymorphism, etc.," NY: Marcel Dekker, Inc., 1999, 1-2, 125-181, 183-226.*
CMU Pharmaceutical polymorphism, intenet p. 1-3 (2002) (printout Apr. 3, 2008).*
Singhal et al., "Drug polymorphism, etc.," Advanced drug delivery reviews 56, 335-347 (2004).*

* cited by examiner

Primary Examiner — Patricia Morris

(57) ABSTRACT

The present invention relates to the trihydrate of pradofloxacin, to a process for its preparation and to antibacterial compositions comprising them.

3 Claims, 2 Drawing Sheets

CRYSTALLINE FORM OF CYANO-1-CYCLOPROPY1-7-1S,6S-2,8-DIAZABICYCLO[4.3.0]NONAN-8-YL)-6-FLUORO-1,4-DIHYDRO-4-OXO-3-QUINOLINE CARBOXYLIC ACID

The present invention relates to the trihydrate of pradofloxacin, to a process for its preparation and to antibacterial compositions comprising it.

The 8-cyano-1-cyclopropyl-7-(1S,6S)-2,8-diazabicyclo[4.3.0]nonan-8-yl)-6-fluoro-1,4-dihydro-4-oxo-3-quinolinecarboxylic acid of the formula (I) will be referred to hereinbelow by its INN (International Non-proprietary Name) as pradofloxacin.

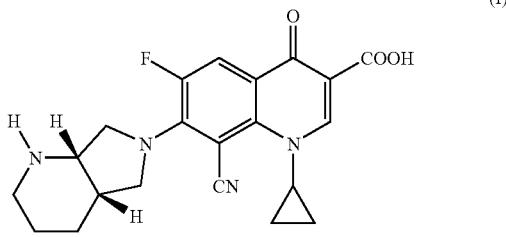
(I)

Pradofloxacin is known from WO 97/31001. According to this, it is prepared by reacting 7-chloro-8-cyano-1-cyclopropyl-6-fluoro-1,4-dihydro-4-oxo-3-quinolinecarboxylic acid with (1S,6S)-2,8-diazabicyclo [4.3.0]nonane in a mixture of dimethylformamide and acetonitrile in the presence of an auxiliary base. After admixing with water, pradofloxacin is extracted with dichloromethane from water and isolated by removing the extractant. This gives a powder which does not have any distinct crystal modification. However, it is a prerequisite for the preparation of medicaments that it is possible for an active ingredient which can be present in different crystal modifications to specify unambiguously in which crystal modification it is used to prepare the composition.

The sometimes amorphous powder which is obtained by the above-outlined preparation process is additionally hygroscopic. However, amorphous solids, and especially hygroscopic solids, are difficult to handle in pharmaceutical processing, since they have, for example, low bulk densities and unsatisfactory flow properties. In addition, special working techniques and equipment is required to handle hygroscopic solids in order to obtain reproducible results, for example with regard to the active ingredient content or the stability in the solid formulations produced.

Defined crystal forms of pradofloxacin are already known: modification A (WO 00/31075), modification B (WO 00/31076), modification C (WO 00/52009) and modification D (WO 00/52010), and also the semihydrochloride (WO 00/31077).

Active ingredients for medicaments should be present in forms which are stable even under unfavourable storage conditions, such as elevated temperature and atmospheric moisture. Changes, for example in the crystal structure are undesired, since these often also change important properties, for example the water solubility. In principle, thermodynamically stable crystalline forms of an active ingredient are therefore being sought.

It is an object of the invention to prepare a thermodynamically stable, defined crystal form of pradofloxacin which is suitable for pharmaceutical formulations owing to its properties.

DETAILED DESCRIPTION OF THE INVENTION

Surprisingly, the thermodynamically very stable, hitherto unknown pradofloxacin trihydrate has now been found.

The invention therefore provides pradofloxacin trihydrate; it can be illustrated by the following formula (II):

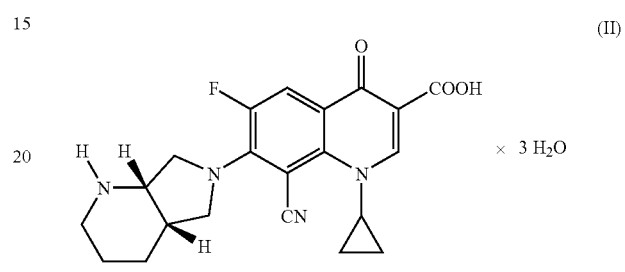
(II)

Pradofloxacin trihydrate has an X-ray powder diffractogram having the reflections (2 theta), reported in the following Table 1, of high and average intensity (>30% relative intensity).

TABLE 1

Reflections of average and high intensity ($I_{Rel} > 30\%$) of pradofloxacin trihydrate:

| 2 θ (2 theta) |
| --- |
| 10.6230 |
| 14.1386 |
| 18.4032 |
| 20.9422 |
| 22.5604 |
| 22.8420 |
| 24.5165 |
| 25.8426 |
| 26.4972 |
| 26.8759 |
| 27.1231 |

Figure 1:
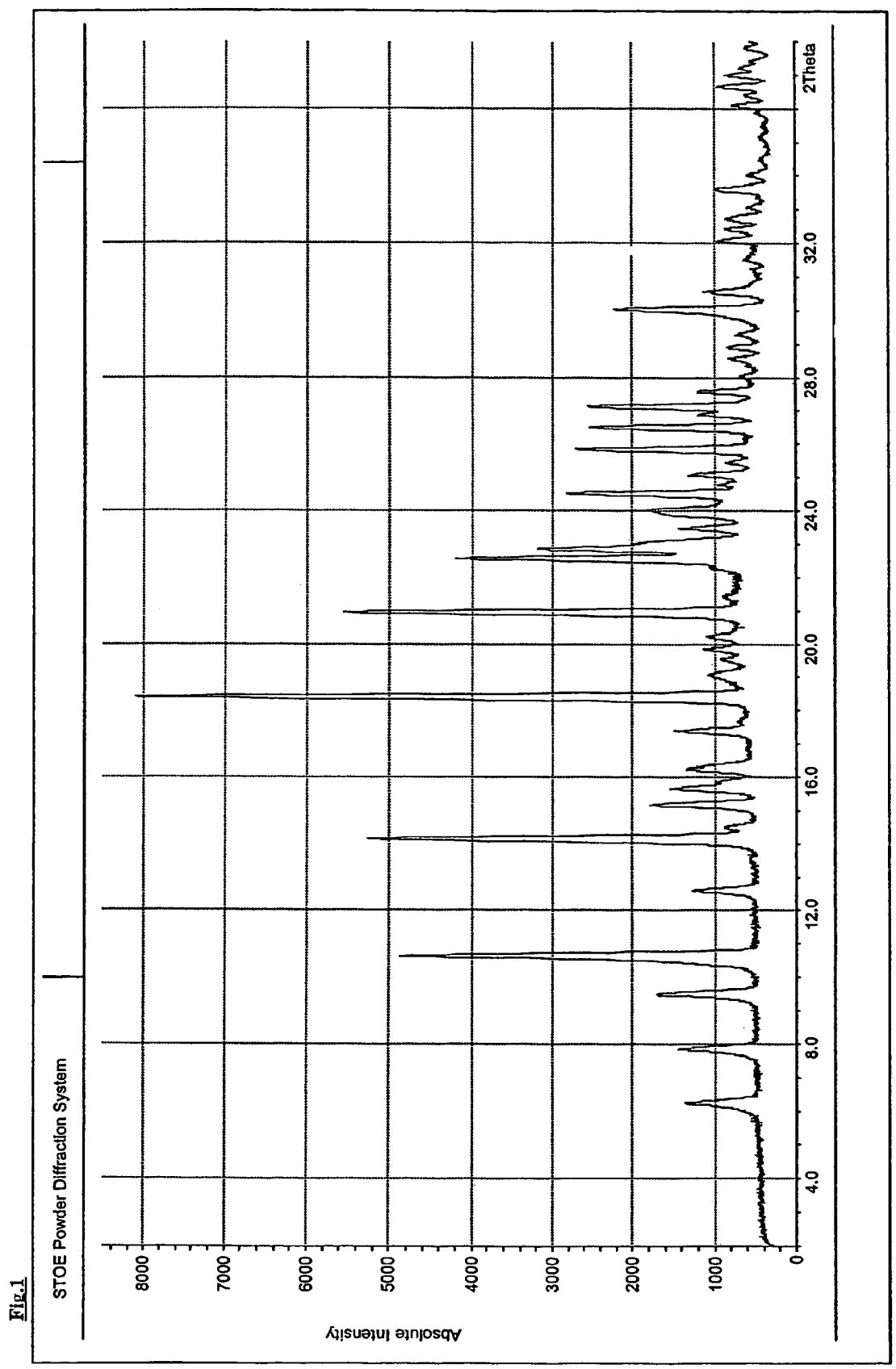
FIG. 1 is the powder X-ray diffractogram of pradofloxacin trihydrate.

The powder X-ray diffractogram of pradofloxacin trihydrate is reproduced in FIG. 1.

In addition, it was possible to characterize pradofloxacin trihydrate by X-ray structural analysis of a single crystal. Characteristic data are:

| | |
| --- | --- |
| Crystal system | monoclinic |
| Space group | $P2_1$ |
| Dimensions of the unit cell | a = 12.4790(18) Å α = 90°. |
| | b = 12.1275(18) Å β = 111.009(6)°. |
| | c = 15.010(2) Å γ = 90°. |
| Volume | 2120.6(5) Å$^3$ |

Figure 2:
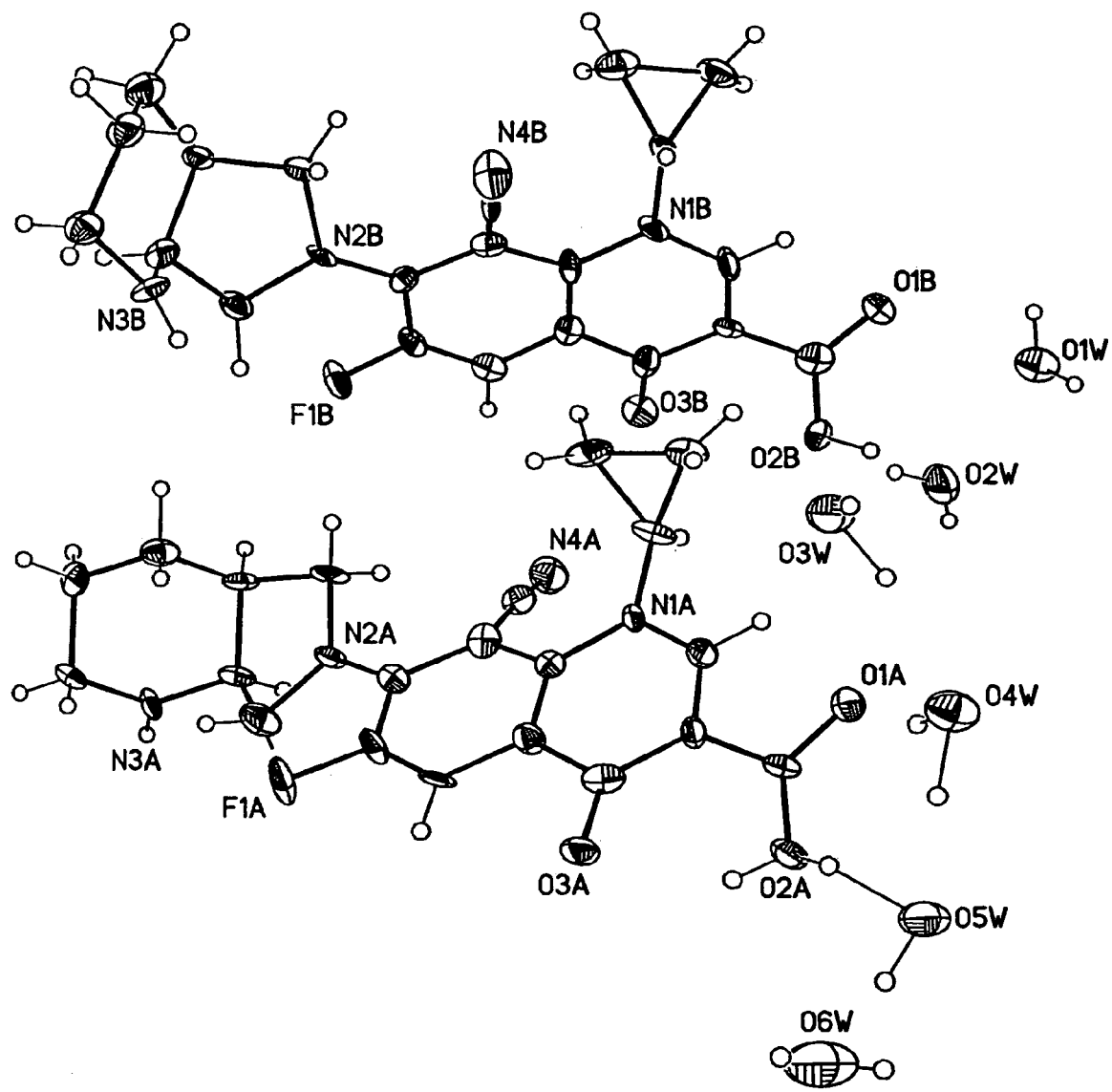
FIG. 2 is the structure of pradofloxacin trihydrate in crystal lattice.

The structure in the crystal lattice is shown in FIG. 2.

Pradofloxacin trihydrate can be prepared by the following processes:

A solution of pradofloxacin in a polar aprotic solvent is heated to a temperature of 50° C. or more and then admixed with water which contains seed crystals of pradofloxacin trihydrate.

The solution in the polar aprotic solvent is added preferably at least to the same volume of water, more preferably to 2 to 4 times the volume. It may be advantageous to further heat the resulting mixture to a temperature in the range of 50° C. to the boiling point.

The polar aprotic solvent used should be miscible with water to a sufficient degree; preferred examples are dimethylformamide (DMF), acetonitrile, propionitrile and in particular N-methylpyrrolidone (NMP). It is also possible to use mixtures of these solvents.

Alternatively, pradofloxacin can be heated in water together with a small amount of pradofloxacin trihydrate, preferably to a temperature in the 50 to 100° C. range.

In addition, pradofloxacin trihydrate may also be obtained by reprecipitation via the salts, in which case pradofloxacin trihydrate seed crystals are appropriately added in the course of neutralization.

In the course of reprecipitation, preference is given to dissolving the pradofloxacin in a suitable acid in the presence of water. The solution is then neutralized to pH 7 with a base and the seed crystals are added.

In all processes, the pradofloxacin trihydrate precipitates out as a solid, if necessary after cooling (for example to room temperature).

If required, seed crystals can be prepared by storing a sample of pradofloxacin of the modification B for a prolonged period at an atmospheric moisture content of at least 97%, typically at room temperature.

Pradofloxacin trihydrate is surprisingly stable and is not converted to other crystal forms even in the course of prolonged storage. In addition, pradofloxacin trihydrate does not show any tendency to take up further water from the air. Finally, it can be purified in a simple manner by crystallization. For these reasons, it is outstandingly suitable for preparing medicament formulations, especially those in which the active ingredient is present as a solid. By virtue of its stability, it imparts to these formulations the desired long-lasting storage stability. It is thus possible with pradofloxacin trihydrate to prepare stable formulations of pradofloxacin in a defined and controlled manner.

Pradofloxacin trihydrate is outstandingly effective against pathogenic bacteria in the field of human or veterinary medicine. The action of pradofloxacin trihydrate and thus also its broad field of use corresponds to those of pradofloxacin.

The X-ray powder diffractogram for the characterization of pradofloxacin trihydrate was obtained with a STADI-P transmission diffractometer (CuK$_\alpha$ radiation) with location-sensitive detector (PSD2) from Stoe.

The X-ray structural analysis of the single crystal was obtained with a Siemens P4 diffractometer, equipped with a SMART-CCD-1000 two-dimensional detector, a rotating anode (MACScience Co.) with MoK radiation, a graphite monochromator and a Siemens LT2 low temperature apparatus (T=−120° C.).

The examples which follow illustrate the invention without restricting it. The conditions used in the examples which follow are particularly preferred.

EXAMPLES

Example A

Recrystallization from NMP/Water

A.1 120 g of pradofloxacin are heated to 75° C. in 960 ml of peroxide-free N-methylpyrrolidone (NMP). This solution is poured through a fluted filter into 2880 ml of water which have been seeded with pradofloxacin trihydrate. The mixture is allowed to come to room temperature without stirring and left to stand at room temperature for one day. The solid is filtered off with suction, washed twice with 100 ml each time of water and dried under air.

Yield: 115.73 g, 84.9% of theory.

A.2 20 g of pradofloxacin are heated to 75° C. in 90 ml of peroxide-free NMP. Afterwards, 270 ml of water are added and the mixture is heated further to 100° C. The resulting solution is kept at this temperature for another 15 minutes, then cooled somewhat and seeded with pradofloxacin trihydrate. For crystallization, the mixture is left to stand overnight. The solid is filtered off with suction, washed twice with a little water and dried under air.

Yield: 20.44 g, 89.9% of theory.

In all cases, according to the X-ray powder images, pradofloxacin trihydrate was obtained.

Example B

Heating in Pure Water 5 g of pradofloxacin and 100 mg of pradofloxacin trihydrate are added to the amount of water specified and heated to the temperature specified for 3 hours.

TABLE 2

Modification conversion by heating in water

| Experiment | Yield | Amount of water | Conditions |
|---|---|---|---|
| B.1 | 91% | 25 ml | 85° C. |
| B.2 | 93% | 50 ml | 85° C. |
| B.3 | 92% | 100 ml | 85° C. |

In all cases, according to X-ray powder images, pradofloxacin trihydrate was obtained.

Example C

Reprecipitation Via Salt

TABLE 3

Reprecipitation of pradofloxacin

| Experiment | Acid | Amount (mmol) | Yield % | Comment |
|---|---|---|---|---|
| C.1 | Sulphuric acid | 6 | 93.5 | Precipitate at acidic pH |
| C.2 | Acetic acid | 6 | 92 | |
| C.3 | Formic acid | 6 | 81.7 | |
| C.4 | Sulphuric acid | 3 | 94.2 | Precipitate at acidic pH |
| C.5 | Acetic acid | 6 | 89.8 | Precipitated at 60° C. and heat-treated for 2 hours. |

In each case, the specified amount of acid is dissolved in 12 ml of water, 2.4 g (6 mmol) of pradofloxacin are added, and the mixture is stirred for 15 minutes and subsequently neutralized to pH 7.0 with conc. ammonia solution. As soon as the solution becomes cloudy, seed crystals of pradofloxacin trihydrate are added. The mixture is stirred at room temperature overnight, then the solid is filtered off with suction and dried under air.

In all cases, according to X-ray powder images, pradofloxacin trihydrate was obtained.

The invention claimed is:
1. A pradofloxacin trihydrate of formula (II)

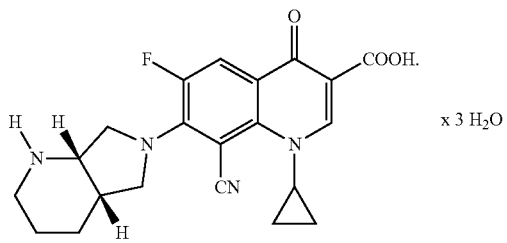

x 3 H₂O (II)

2. The pradofloxacin trihydrate of claim 1, having an X-ray powder diffractogram having the reflections

| 2θ (2 theta) |
| --- |
| 10.6230 |
| 14.1386 |
| 18.4032 |
| 20.9422 |
| 22.5604 |
| 22.8420 |
| 24.5165 |
| 25.8426 |
| 26.4972 |
| 26.8759 |
| 27.1231 | of high and average intensity (>30% relative intensity).

3. The pradofloxacin trihydrate of claim 1, wherein the crystal system is monoclinic, the space group is P2$_1$, the dimensions of the unit cell are a=12.4790(18) Å α=90°, b=12.1275(18) Å β=111.009(6)°, c=15.010(2) Å γ=90°, and the volume is 2120.6(5) Å$^3$.